(12) United States Patent
Erlanson-Albertsson

(10) Patent No.: US 7,425,577 B2
(45) Date of Patent: Sep. 16, 2008

(54) LIPASE-COLIPASE INHIBITOR

(75) Inventor: Charlotte Erlanson-Albertsson, Göteborg (SE)

(73) Assignee: Forskarpatent 1 SYD AB, Lund (SE)

( * ) Notice: Subject to any disclaimer, the term of this patent is extended or adjusted under 35 U.S.C. 154(b) by 265 days.

(21) Appl. No.: 11/358,772

(22) Filed: Feb. 21, 2006

(65) Prior Publication Data

US 2006/0199869 A1 Sep. 7, 2006

Related U.S. Application Data

(63) Continuation of application No. PCT/SE2004/001216, filed on Aug. 19, 2004.

(30) Foreign Application Priority Data

Aug. 21, 2003 (SE) .................................. 0302253

(51) Int. Cl.
*A61K 31/24* (2006.01)

(52) U.S. Cl. ..................................... 514/538; 514/909

(58) Field of Classification Search ................. 514/538, 514/909
See application file for complete search history.

(56) References Cited

U.S. PATENT DOCUMENTS

| | | | | |
|---|---|---|---|---|
| 4,032,658 A | * | 6/1977 | Beregi et al. ................. | 514/538 |
| 4,062,764 A | * | 12/1977 | White et al. ................. | 208/348 |
| 4,490,455 A | * | 12/1984 | Hoffend et al. ........... | 430/108.2 |
| 4,588,843 A | * | 5/1986 | Marlett ........................ | 564/508 |
| 5,494,894 A | * | 2/1996 | Erlanson-Albertsson ..... | 514/12 |

FOREIGN PATENT DOCUMENTS

WO WO98/30588 7/1998

* cited by examiner

*Primary Examiner*—Kevin E. Weddington
(74) *Attorney, Agent, or Firm*—Gauthier & Connors LLP

(57) ABSTRACT

The present invention relates to novel colipase-lipase inhibitors of the general formulae to be used in the treatment of prophylaxis of obesity, as well as pharmaceutical compositions containing the same, and method for treating obesity using said compounds.

7 Claims, 14 Drawing Sheets

LIPASE-COLIPASE INHIBITOR

This is a continuation of copending application International Application PCT/SE04/001216 filed on 19 Aug. 2004 and which designated the U.S.

DESCRIPTION OF THE PRIOR ART

TECHNICAL FIELD

The present invention relates to a new group of therapeutically active organic compounds useful in particular as inhibitors of the lipase-colipase system for the prevention of obesity.

BACKGROUND OF THE INVENTION

Lipases is a group of enzymes taking part in the digestion of fat by hydrolysing lipids present in the food thereby allowing absorption of the fat by the intestinal tract. The lipases are mainly three, viz gastric lipase, pancreatic lipase and carboxylic ester lipase.

Pancreatic lipase is the main enzyme responsible for the hydrolysis of triacylglycerols in the diet. The pancreatic lipase is a typical lipase catalysing the hydrolysis of water-insoluble substrates forming an interface. The enzyme is said to be activated by interfaces.

The most peculiar property of lipase is that the activity is strongly inhibited by surface active agents like the naturally occurring bile salts. To overcome this nature has come to use another pancreatic protein, colipase.

Colipase binds to lipase in a 1:1 molar ratio and also binds to the bile-salt covered triacylglycerol interface in this way anchoring lipase to its triacylglycerol substrate. Colipase as such has no lipolytic activity.

Colipase is formed by pancreas and is excreted as a procolipase.

It has been established that mice deficient in procolipase and fed a high fat diet will have cholesterol, triglyceride, glucose and insulin concentrations in blood serum at about the same levels as mice fed on low fat diet. (D'Agostino, D. et al., J. Biol. Chem. vol 277, no. 9, pp 7170-7177 (2002)).

Obesity has in recent days become an ever increasing problem to population of the industrialized world, whereby e.g., the average weight of a male at the age of 20 has increased with about 10 kilogrammes during the last 20 years. Obesity leads to the formation of the so-called metabolic syndrome, to which diabetes and cardio-vascular diseases belong. The worst forms of obesity are visceral fat accumulation, liver fat accumulation and even muscular fat accumulation.

The high fat intake or over intake of fat is due to a number of factors, such as too much sitting still, too much of fat rich food (so called "junk food"), and an erroneous diet information. It is also a relic of old days tradition of having a large calorie intake due to a heavier workday.

Food of today does not provide a long-term feeling of satisfaction either, which in turn leads to an increased food intake. However, a lipid diet remaining in the intestine will increase the feeling of satisfaction for a longer time period, and thus there is a desire having lipids remaining in the intestines to satisfy the demand from the brain. One way of preventing obesity is by administering a preparation under the trademark XENECAL®, which is a lipase inhibitor in general.

U.S. Pat. No. 4,588,843 discloses a synthesis of (alkoxy-alkyl)amines, whereby the compound explicitly prepared is 2-(dimethylamino)ethyl dodecyl ether. The compound is said to have a use as an intermediate for lubricating oil additives, such as detergent-dispersants and pour point depressants, soap and detergent products, such as surface active agents, and foam stabilizers, extenders for polymers, such as polyurethanes and epoxy resins, agricultural chemicals, such as herbicides, fungicides, plant growth regulators, insecticides, vermicides, miticides, and the like. No pharmaceutical use is proposed.

The main object of the present invention is to provide a therapeutically active compound which inhibits pancreatic lipase-colipase action, thereby reducing digestion of lipids from the diet, thereby preventing obesity in general by reduced lipid absorption.

Another object is to obtain a situation in the intestines where diet lipid/fat remains in the intestines providing a basis for a better feeling of satisfaction, thereby avoiding an over-intake of food.

SUMMARY OF THE INVENTION

It has now been found possible to meet these requirements by means of the present invention, which offers a group of compounds to be used in the manufacture of therapeutically active preparations for the treatment of obesity.

The group of compounds is defined by the following general formulae

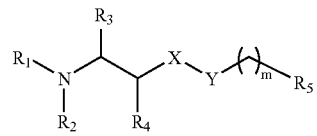

wherein $R_1$ and $R_2$ each independently is hydrogen, or lower alkyl, $R_3$ and $R_4$ each independently is hydrogen, or lower alkyl, X is —O—, —C—, or —S—, Y is a covalent bound or is [—$CH_2$—$CH_2$—O—]$_x$, wherein x is an integer from 0 to 8, preferably 0 to 5, m is an integer from 0 to 30, preferably 4 to 16, more preferably 4 to 12, $R_5$ is hydrogen, $CH_3$ or $CF_3$, whereby when $R_1$ and $R_2$ are each methyl, X is —O—, Y is a covalent bond, $R_5$ is $CH_3$ m is not 11, or when $R_1$ and $R_2$ are each methyl, X is —O—, Y is a covalent bond $R_5$ is hydrogen, m is not 12.

Lower alkyl $R_1$ and lower alkyl $R_2$ mean a lower, straight or branched alkyl group having up to 7 carbon atoms in the chain, preferably up to 4 carbon atoms, more preferably up to 2 carbon atoms. $R_1$ and $R_2$ will thus mean each independently methyl, ethyl, n-propyl, isopropyl, n-butyl, sec-butyl, isobutyl, and tert-butyl. $R_1$ and $R_2$ may also be the same or different. $R_1$ and $R_2$ are preferably each methyl and/or ethyl.

Lower alkyl $R_3$ and lower alkyl $R_4$ mean a lower, straight or branched alkyl group having up to 7 carbon atoms in the chain, preferably up to 4 carbon atoms, more preferably up to 2 carbon atoms. $R_3$ and $R_4$ will thus mean each independently methyl, ethyl, n-propyl, isopropyl, n-butyl, sec-butyl, isobutyl, and tert-butyl. $R_3$ and $R_4$ may also be the same or different.

$R_3$ and $R_4$ are each preferably hydrogen.

X is oxygen or sulphur, preferably oxygen.

Y denotes a covalent bound or the group [—$CH_2$—$CH_2$—O—]$_x$, which latter thus denotes a polyethylene glycol chain having up to 8 moieties, preferably up to 5 moieties. However, x is preferably 0 (zero). x is thus the integer 0, 1, 2, 3, 4, or 5.

The integer m is 0 to 30, thus the group —$(CH_2)_m$—$CH_3$ can comprise up to 31 carbon atoms. This group having up to 31 carbon atoms is straight or branched, preferably straight. m is preferably up to 11, more preferably up to 7, most preferably up to 3. m is thus the integer 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In a preferred embodiment X, Y, $(CH_2)_m$ and $R_5$ together comprises at least 8 carbon atoms.

In a further preferred embodiment the chain —$(CH_2)_m$— comprises one or more double or triple bonds, whereas the number of hydrogen atoms may be less than 2m, and can thus be 2m−2, 2m−4, 2m−6, in cases of one, two or three triple bonds, or 2m−4, 2m−8, or 2m−12 in case of one, two or three triple bonds. In case of double bonds and triple bonds, i.e. unsaturation, stereo Isomeric forms may be present. Thus racemic as well as stereo isomeric pure compounds will exist.

In a further aspect of the invention it encompasses the use of a compound defined by the following general formulae

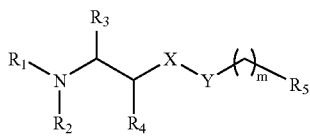

wherein $R_1$ and $R_2$ each independently is hydrogen, or lower alkyl, $R_3$ and $R_4$ each independently is hydrogen, or lower alkyl, X is —O—, —C— or —S—, Y is a covalent bound or is [—$CH_2$—$CH_2$—O—]$_x$, wherein x is an integer from 0 to 8, preferably 0 to 5, m is an integer from 0 to 30, preferably 4 to 16, more preferably 4 to 12, $R_5$ is hydrogen, $CH_3$ or $CF_3$, in the preparation of a pharmaceutical composition for the inhibition of colipase-pancreatic lipase controlled digestion of lipids in the intestine, in order to prevent and/or reduce obesity.

In particular the invention encompasses the following compounds and their use:

2-(Dimethylamino)-ethyl-stearyl ether
2-(Dimethylamino)-ethyl-tetradecyl ether
2-(Dimethylamino)-ethyl-oleyl ether
2-(Dimethylamino)-ethyl-linolyl ether
2-(Dimethylamino)-ethyl-dodecyl ether
2-(Dimethylamino)-ethyl-octyl ether
2-(Diethylamino)-ethyl-stearyl ether
2-(Diethylamino)-ethyl-oleyl ether
2-(Diethylamino)-ethyl-linolyl ether
2-(Diethylamino)-ethyl-dodecyl ether
2-(Diethylamino)-ethyl-octyl ether
2-(Diisopropylamino)-ethyl-stearyl ether
2-(Diisopropylamino)-ethyl-oleyl ether
2-(Diisopropylamino)-ethyl-linolyl ether
2-(Diisopropylamino)-ethyl-dodecyl ether
2-(Diisopropylamino)-ethyl-octyl ether
2-(Dimethylamino)-ethyl-pentaethyleneglycol-stearyl ether
2-(Dimethylamino)-ethyl-pentaethyleneglycol-linolyl ether
2-(Dimethylamino)-ethyl-pentaethyleneglycol-oleyl ether
2-(Dimethylamino)-ethyl-pentaethyleneglycol-dodecyl ether
2-(Dimethylamino)-ethyl-pentaethyleneglycol-octyl ether
2-(Dimethylamino)-ethyl-pentaethyleneglycol butyl ether
2-(Dimethylamino)-ethyl-pentaethyleneglycol methyl ether
2-(Dimethylamino)-ethyl-pentaethyleneglycol ethyl ether
2-(Dimethylamino)-ethyl-triethyleneglycol-dodecyl ether
2-(Dimethylamino)-ethyl-triethyleneglycol-octyl ether
2-(Dimethylamino)-ethyl-triethyleneglycol butyl ether
2-(Dimethylamino)-ethyl-triethyleneglycol methyl ether
2-(Dimethylamino)-ethyl-triethyleneglycol ethyl ether
2-(Dipropylamino)-ethyl-octaethyleneglycol dodecyl ether
2-(Dimethylamino)-ethyl-octaethyleneglycol dodecyl ether
2-(Diethylamino)-ethyl-octaethyleneglycol dodecyl ether
N,N-dimethyl hexadecyl amine
N,N-dimethyl tetradecyl amine
N,N-dimethyl dodecyl amine

DESCRIPTION OF THE PRESENT INVENTION

The compounds of the present invention are prepared in accordance with the following example.

Preparation of Dimethylaminoethyl Dodecyl Ether

Materials

Dimethylethanolamine

Dodecylchloride

Sodium

Sodium was melted during reflux in toluene as a solvent. When all sodium had reacted the dimethyl ethanolamine is added dropwise and is allowed to boil while stirred over the night. The sodium chloride formed is filtrated off, while the dimethylaminoethyl dodecyl ether is present in the solution. The solution is evaporated in vacuo. The product is then dissolved in heptane, and is extracted using 50% methanol to remove unreacted dimethyl ethanolamine. The reaction mixture is evaporated in vacuo and will now contain the desired product as well as unreacted dodecylchloride. The product is dissolved in heptane and is purified by means of silica gel chromatography. The purity of the product is determined using thin layer chromatography.

Refraction indexes and melting points of some of the compounds prepared are:

| Compound | RI | Melting point (° C.) |
| --- | --- | --- |
| N,N-dimethyltetradecyl amine | 1.441 | 0 to 20° C. |
| Dimethylaminoethyl dodecyl ether | 1.439 | 0 to 20° C. |
| Dimethylaminoethyl octyl ether | 1.425 | <−20° C. |

The present compounds can be tested in different models, in vitro and in vivo. Below one in vitro model and one in vivo model are described, by means of which the present compounds have been tested. Relevant data are shown as well.

In Vitro

Determination of Lipolysis by Colipase/Lipase

The most important enzyme in the gastro-intestinal tract being responsible for the hydrolysis of lipids/fats in the gastro-intestinal tract is lipase, pancreatic lipase, together with its protein cofactor colipase. These are two proteins, which are secreted from the pancreatic gland. The lipase is totally inactive without colipase in the environment the intestine forms, wherein the lipids/fat is emulsified by means of bile acids. The colipase binds to lipase in a molar 1:1 complex and then moves the complex to the triglyceride surface. In the binding between lipase and colipase hydrogen bonds are present, between arg38 of the colipase and ser343 of the lipase and from glu15 of the colipase and the asn241 of the lipase molecules. In the binding of colipase to the substrate (the lipids/fat) there are both hydrophobic bonds as well as ion-ion bonds present. By an isolated lack of colipase it has been shown that colipase has a decisive role for the lipolysis in the gastro-intestinal tract of humans. Pure lipase and colipase have been produced in accordance with the following.

Materials

Tributyrine

NaTDC (sodium taurodeoxycholate)

Lipase, Purified from Human Pancreatic Gland

Colipase, Purified from Human Pancreatic Gland

Method 0.5 ml of tributyrine is mixed with 15 ml of a buffer containing 1 mM $CaCl_2$, 150 mM NaCl, 2 mM tris-maleate, pH 7.0 and 4 mM NaTDC (sodium taurodeoxycholate). An emulsion is obtained by continuous stirring. pH is titrated by means of a pH-state, where 0.1 N NaOH is added automatically to keep an constant pH. 10 µl of lipase is added from a stock solution containing 70 units of lipase/ml, followed by 10 µl of colipase from a stock solution containing 1 mg colipase/ml. An activity is registered which is determined to be 100%. An addition of an inhibitor is then made. A new assay is used for every concentration, prepared in the same way. The inhibition is registered as percentage of control. A dose-response plot is obtained for the compounds having an inhibiting ability.

The inhibiting effect in the in vitro model given above of different compounds of the invention is given in Table 1 below.

TABLE 1

| Amount of inhibitor (µmol) | Activity Control (µmol/min) | Activity Inhibitor (µmol/min) |
|---|---|---|
| A. Compound dimethylaminoethyl octyl ether. | | |
| 0 | | |
| 2.49 | 0.304 | 0.249 |
| 4.98 | 0.319 | 0.215 |
| 8.71 | 0.314 | 0.136 |
| 12.44 | 0.356 | 0.069 |
| 18.66 | 0.32 | 0.053 |
| 21.89 | 0.293 | 0.035 |
| 24.88 | 0.278 | 0 |
| B. Compound dimethylaminoethyl dodecyl ether. | | |
| 0 | | |
| 0.97 | 0.313 | 0.237 |
| 1.95 | 0.301 | 0.204 |
| 3.89 | 0.308 | 0.127 |
| 6.81 | 0.319 | 0.069 |
| 9.73 | 0.327 | 0.033 |
| 14.59 | 0.328 | 0.013 |
| 19.46 | 0.332 | 0 |
| C. Compound dimethylaminoethyl pentaethyleneglycol dodecyl ether. | | |
| 0 | | |
| 0.26 | 0.307 | 0.273 |
| 0.52 | 0.29 | 0.236 |
| 1.05 | 0.302 | 0.222 |
| 2.62 | 0.299 | 0.13 |
| 5.23 | 0.314 | 0.083 |
| 7.85 | 0.312 | 0.04 |
| 10.46 | 0.3 | 0.015 |
| 15.69 | 0.319 | 0.009 |
| 20.92 | 0.282 | 0 |
| D. Compound dipropylaminoethyl octaethyleneglycol dodecyl ether. | | |
| 0 | | |
| 0.2 | 0.256 | 0.256 |
| 0.4 | 0.28 | 0.256 |
| 0.8 | 0.259 | 0.209 |
| 2.01 | 0.25 | 0.136 |
| 4.02 | 0.246 | 0.096 |
| 8.04 | 0.244 | 0.033 |
| 12.06 | 0.252 | 0.011 |
| 16.08 | 0.247 | 0 |
| E. Compound N,N-dimethyl tetradecyl amine | | |
| 0 | | |
| 1.04 | 0.226 | 0.179 |
| 2.07 | 0.243 | 0.121 |
| 4.14 | 0.223 | 0.056 |
| 7.25 | 0.257 | 0.045 |
| 10.35 | 0.282 | 0.033 |
| 15.53 | 0.256 | 0 |

As evident from above the compounds tested all possess an inhibiting activity in the test model given.

In Vivo

Method

Sprague-Dawley rats weighing 200-220 g, stored in cages using a 12 hours of light/12 hours of darkness cycle were used. They had free admittance to food and water prior to the test. The day prior a test the rats were fasted, and were anaesthetised in the morning using diethyl ether. 1 ml of Intralipid (200 mg/ml) with and without inhibitor was fed to the rats by means of a syringe through the mouth and ending in the stomach. Blood samples were taken at time 0, prior to the test start, and then after 30, 60, 120 and 180 minutes after feeding with Intralipid. After centrifugation, serum was separated and stored at −20° C. for analysis. Analyses of free fatty acids, triglycerides and total cholesterol were made. The test has been repeated, also using different dosages of the inhibitors tested.

The results show, as evident from Table 2 below, an inhibition of the absorption of fat to the blood circulation determined as triglycerides and fatty acids concentrations.

TABLE 2

In vivo experiments in accordance with the in vivo protocol given herein, in rat showing effect on concentration of free fatty acids and triglycerides in blood serum against control.

| Inhibitor | Free fatty acids (mmol) | | | | | Triglycerides (mg/dl) | | | | |
|---|---|---|---|---|---|---|---|---|---|---|
| | 0 | 30 | 60 (min) | 120 | 180 | 0 | 30 | 60 (min) | 120 | 180 |
| Control | 0.60 | 0.92 | 1.05 | 0.95 | 0.85 | 96 | 111 | 109 | 130 | 95 |
| Compound C12* | 0.56 | 0.63 | 0.70 | 0.60 | 0.62 | 103 | 95 | 98 | 95 | 77 |
| Control | 0.61 | 0.78 | 0.84 | 0.94 | 0.72 | | | n.d.** | | |
| Compound C12 | 0.57 | 0.67 | 0.72 | 0.72 | 0.74 | | | n.d. | | |

*Compound C12 is dimethylaminoethyl dodecyl ether.
**n.d. means not determined.

The results show, as evident from Table 3 below, a dose dependent inhibition of the absorption of fat to the blood circulation determined as fatty acids concentrations.

TABLE 3

Compound dimethylaminoethyl dodecyl ether in dose-response evaluation.

| Dose of active compound (µg) | Free fatty acids (mol/l) | Free fatty acids (% of control) |
|---|---|---|
| 0 | 1.45 | 100 |
| 10 | 1.25 | 83.7 |
| 50 | 0.83 | 56.1 |
| 100 | 0.85 | 57.4 |
| 200 | 1.1 | 74.3 |

The conclusion is that the inhibitors of the present invention have effects both in in vitro as well as in in vivo systems, which can be expected provide for a great potential at the treatment of high blood lipid levels, diabetes type 2 and obesity.

In a further aspect of the invention the compounds disclosed above are used in the manufacture of pharmaceuticals for reducing appetite, in order to reduce obesity.

In the first experiment, the effects of orally administered dimethylaminoethyl dodecyl ether (shortened dimaele in Figures) for 5 days on food intake and blood lipids was examined in female Sprague-Dawley rats. A single dose of dimethylaminoethyl dodecyl ether administration (50 µl) through a gastric gavage to rats that had been fed with high-fat diet resulted in a highly significant reduction in food intake. The reduction of food intake was accompanied with the decreased body weight in these rats fed with high-fat diet. However, dimethylaminoethyl dodecyl ether failed to decrease food intake in rats fed with low-fat diet. Blood lipids analysis has shown that dimethylaminoethyl dodecyl ether decreased serum triglyceride and fatty acids, but this was not statistic significance. Dimethylaminoethyl dodecyl ether had no effect on plasma cholesterol levels. Furthermore, we have measured that serum peptide $YY_{3-36}$, released from the gastrointestinal tract postprandially in proportion to the calorie content of a meal. There was no difference of serum $PYY_{3-36}$ levels in rats received dimethylaminoethyl dodecyl ether compared to the control rats (0.85±0.26 ng/ml vs. 0.86±0.24 ng/ml). Serum leptin levels markedly decreased in dimethylaminoethyl dodecyl ether-treated rats, whereas serum ghrelin levels were increased when compared with the control group. At the end of experiment, pancreatic lipase activity and protein expression were determined following infusion of dimethylaminoethyl dodecyl ether for 5 days. Pancreatic lipase activity was not changed in dimethylaminoethyl dodecyl ether-treated rats, but the lipase protein expression was slightly reduced when compared to the control rats. A second experiment was subsequently undertaken to investigate whether oral administration of dimethylaminoethyl dodecyl ether would affect blood lipids levels as well. Rats that have been deprived of food for 17 h were orally given with either Intralipid (200 mg/ml) or dimethylaminoethyl dodecyl ether (200 µl) plus Intralipid. Blood samples were colleted at 0, 30, 60, 120 and 180 min after administration. Dimethylaminoethyl dodecyl ether significantly reduced plasma triglycerides and fatty acids levels during the test period of 180 min. Thus, the potential use of this inhibitor as a therapeutic tool against hyperlipidaemia and obesity was emerging by the effectiveness of reduction in body weight and food intake. In the current experiment, we will investigate the effect of colipase inhibitor on the activity and expression of pancreatic lipase from rats fed with a high-fat diet.

Introduction
Materials and Methods

Animal

Female female Sprague-Dawley rats were used for all experiments. Rats were housed in a temperature-controlled room (22±1° C.) under a 12-h light (6:00-18:00)/12-h cycle, given free access to water, and fed an libitum on a standard chow unless otherwise stated for a high-fat diet experiment. All procedures using animals were approved by the local ethics committee and followed the guidelines for experiments in animals (European Economic Community Council Directive 86/609/EEC).

Evauluation of Food Intake

For measurement of food consumption rats were individually housed in cage and given a high-fat diet for a week before the beginning of the experiment. The high-fat diet consisted of 16.4% protein, 25.6% carbohydrates and 58.0% fat with a caloric density of 23.6 kJ/g. Rat with as libitum access to high-fat food were orally given dimethylaminoethyl dodecyl ether (37.5 or 50 µl dissolved in 1% methycellulose) through a gastric gavage or 1% methyl cellulose at the onset of the dark cycle (18:00) and food intake was measured at 15 h following dimethylaminoethyl dodecyl ether administration from pre-weighed portions of food dispensed from were cage top. Cages were carefully monitored for evidence of food spillage or grinding.

Blood Lipids Analysis

Blood was drawn in rats from the intra-orbital bullar plexus under anaesthesia and collected in ice-cold tubes. Serum was obtained by centrifugation at 3000 g for 15 min at 4° C. For acute effect of dimethylaminoethyl dodecyl ether on blood lipids, overnight-fasted rats were given 200 µl dimethylaminoethyl dodecyl ether plus 1 ml (200 mg) Intralipids orally through a gastric gavage and blood collected at 0, 30, 60, 120 and 180 min. Plasma triglycerides was determined with an Sigma diagnostics kit. Plasma fatty acids were measured by NEFAC kit (Wako chemicals GmbH, Neuss, Germany). Plasma PYY (3-36) and leptin were measured with the PYY Enzyme Immunossay kit and leptin Enzyme Immunossay (Phoenix Pharmaceuticals, USA)

Pancreatic Lipase Activity and Expression

At the end of experiment, rats were killed and the pancreas collected for assay of lipase activity and protein expression. Lipase activity was determined with pH stat titration (Mettle Components DK 10, DK 11, DV11) using tributyrin dispersed in bile salt as substrate (Borgström & Erlanson). Lipase expression was analysed by western blot.

Western Blot Analysis

Pancreas was homogenized in 0.5% digitonin buffer containing 10 mM sodium phosphate (pH6.0) and 1 mini complete tablet on ice. After centrifuge at 14000 g, 4° C. for 10 min, the supernatant was collected and heating at 65° C., 15 min for inactivate endogenous lipase. The protein amount was measured by BCA method. Equal amount (50 µg) protein was load on 10% SDS-polyacrylamide gels, transferred to the nitrocellulose membranes and then incubated with anti-lipase antibody in the dilution 1:1000 at 4° C. overnight. Pancreatic lipase protein was detected using a horseradish peroxidase-conjugated donkey anti-rabbit antibody (1:8000) for 60 min at room temperature followed with an enhanced chemiluminescence (Pierce).

Statistics

Stat View program was used for statistics analysis. The data were analyzed using two-way ANOVA followed by post hoc tests for comparison of individual differences. Student's t-test was used for the analysis of triglycerides, $PYY_{3-36}$, leptin and ghrelin data.

Results

Inhibition of Lipase Activity In Vitro Assay

Dimethylaminoethyl dodecyl ether, a colipase inhibitor, inhibited lipase activity in a dose-depended manner, when using tributyrin or intralipid as the substrates (FIGS. 1A and 1B). The maximum inhibition was seen at the dose of 40 µmol and 80 µmol for tributyrin and Intralipid as substrates, respectively.

Reduction of High-fat Food Intake and Body Weight

Food intake was measured in dimethylaminoethyl dodecyl ether and vehicle-treated rats fed with a high-fat diet. In rats given with 50 µl dimethylaminoethyl dodecyl ether, food intake was significantly inhibited at 1 day after administration. This inhibition was maintained up to the 5 days after dimethylaminoethyl dodecyl ether treatment as seen in FIG. 2A (Two-way ANOVA, p<0.001). In rats received 37.5 µl dimethylaminoethyl dodecyl ether, a trend towards reduced food intake was observed, however this did not reach statistic significance (FIG. 2B). When rats were orally given with 25 µl dimethylaminoethyl dodecyl ether, there was no food intake inhibition. In rats fed with a low-fat diet, food intake during the 5 testing days in dimethylaminoethyl dodecyl ether-treated rats was similar to the controls at the doses of 37.5 and 50 µl (FIG. 3). A daily administration of dimethylaminoethyl dodecyl ether (50 µl) for 5 days produced significantly loss of body weight in rats compared with the non-dimethylaminoethyl dodecyl ether treatment group as shown in FIG. 4.

Reduction of Serum Triglyceride, Fatty Acids and Cholesterol Levels

Serum triglyceride, NEFA and cholesterol levels were determined in rats treated with dimethylaminoethyl dodecyl ether for 5 days. As seen in FIGS. 5A and 5B, serum triglycerides and fatty acids levels were decreased after administration of dimethylaminoethyl dodecyl ether (50 µl) for 5 days, this reduction was statistic significance (p<0.05). However, there was no difference in serum cholesterol levels between dimethylaminoethyl dodecyl ether (50 µl) and vehicle-treated rats at 5 day after treatment (data not shown).

Changes in Serum $PYY_{3-36}$, Leptin and Ghrelin

To investigate the potential mechanism by which dimethylaminoethyl dodecyl ether inhibited high-fat food intake and decreased body weight, we have determined gut hormone peptide $YY_{3-36}$ and appetite regulating peptides including leptin and ghrelin. In fasted rats treated with dimethylaminoethyl dodecyl ether (50 µl) for 5 days, serum $PYY_{3-36}$ levels was similar to the controls (FIG. 6A), but serum leptin levels are significantly decreased in dimethylaminoethyl dodecyl ether-treated rats (FIG. 6B). By contrast, serum ghrelin levels are markedly increased when rats were orally given dimethylaminoethyl dodecyl ether for 5 days (FIG. 6C).

Pancreatic Lipase Activity and Protein Expression

Since dimethylaminoethyl dodecyl ether as a colipase inhibitor completely inhibited lipase activity in vitro assay as seen in FIG. 1. We have also determined the lipase activity and protein expression in vivo In rats when administed dimethylaminoethyl dodecyl ether (50 µl) for 5 days through a gastric gavage. Pancreatic lipase activity in dimethylaminoethyl dodecyl ether-treated rats was similar to controls (p>0.05), but the protein expression was reduced in dimethylaminoethyl dodecyl ether group when compared to the control rats (FIG. 7).

Acute Effect of Dimethylaminoethyl Dodecyl Ether on Serum Triglycerides, Fatty Acids and Cholesterol Levels For comparison to the reduction of serum triglycerides and fatty acids from rats orally administered with dimethylaminoethyl dodecyl ether for 5 days, rats received a single dose of dimethylaminoethyl dodecyl ether (200 µl) infusion plus 1 ml Intralipid (200 mg) or Intralipid alone through a gastric gavage. Serum triglycerides levels were significantly reduced at 0, 30, 60, 120 and 180 min after infusion (FIG. 8A, p<0.05). Furthermore, dimethylaminoethyl dodecyl ether infusion decreased serum fatty acids concentrations measured at 0, 30, 60, 120 and 180 min time points as shown in FIG. 8B.

In a still further aspect of the invention the compounds disclosed above are used in the manufacture of pharmaceuticals for reducing the expression of pancreatic lipase, in order to reduce obesity.

Pharmaceutical Formulations

When employed as pharmaceuticals, the compounds of this invention are usually administered in the form of pharmaceutical compositions. These compounds can be administered by a variety of routes including oral, and rectal. These compounds are effective as oral compositions. Such compositions are prepared in a manner well known in the pharmaceutical art and comprise at least one active compound.

This invention also includes pharmaceutical compositions, which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatine capsules, suppositories, and packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatine, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavouring agents. The compositions of the invention can be formulated so as to provide quick, sustained or delayed release of the active ingredient after administration to the patient by employing procedures known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of Formula (I) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. For example, when the drug is administered via the oral route, each dosage contains from about 1 mg to about 1000 mg, preferably about 2 mg to about 500 mg, more preferably about 5 mg to about 100 mg, even more preferably about 5 mg to about 60 mg, of the active ingredient. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like. From a principle point of view the formulation should be administered simultaneously with a food intake, and should then be administered in an amount providing a sufficient inhibition of lipids. Thus the body may need some lipids from a nutritional point of view and this may then influence the amount of inhibiting compounds of the invention administered. The effect of the compounds of the invention takes place in the small intestine and thus there is no further effect obtained as such, but of possible metabolites of the compounds.

For preparing solid compositions such as tablets, the principal active ingredient is mixed with a pharmaceutical excipient to form a solid preformulation composition containing a homogeneous mixture of a compound of the present invention. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation is then subdivided into unit dosage forms of the type described above containing the active ingredient of the present invention.

The tablets, pills or granules of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The tablets, pills or granules of the present invention may be coated with a sustained release coating enabling release at pancreas, where the pancreatic lipase is set free to the intestine. Such a sustained release coating will thus allow for a small release, if any, in the stomach, but allow for total release in the upper part of the small intestine.

For example, a tablet may be prepared by compression or moulding. Compressed tablets may be prepared by compressing in a suitable machine a composition of the invention in a free-flowing form such as powder or granules, optionally mixed with a binder, a lubricant, an inert diluent, and/or a surface active or dispersing agent. Moulded tablets may be made by moulding in a suitable machine, a mixture of the powdered compound moistened with an inert liquid diluent.

In a preferred embodiment, at least one pharmaceutically acceptable excipient is a binder, a filler, or a mixture thereof. Suitable excipients include lubricants, disintegrants, and mixtures thereof. Preferred excipients include, but are not limited to, lactose, croscarmellose, microcrystalline cellulose, pre-gelatinised starch, and magnesium stearate.

Binders suitable for preparing dosage formulations of the pharmaceutical compositions of the invention include, but are not limited to, corn starch, potato starch, or other starches, gelatine, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinised starch, hydroxypropyl methyl cellulose, (e.g., Nos. 2208, 2906, 2910), microcrystalline cellulose and mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, of Marcus Hook, Pa.). A particularly suitable binder is a mixture of microcrystalline cellulose and sodium carboxymethyl cellulose sold as AVICEL RC-581 by FMC Corporation.

Examples of suitable fillers for use with the dosage forms of the compounds of the invention include, but are not limited to, talc, calcium carbonate (e.g., granules or powder), microcrystalline cellulose, powdered cellulose, dextrates, kaolin, mannitol, salicylic acid, sorbitol, starch, pre-gelatinised starch, and mixtures thereof.

Typically, from about 50 to about 99 weight percent of a solid dosage form of the invention is binder and/or filler.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the compound of the invention from the dosage form. Thus, a sufficient amount of disintegrant that is neither too little nor too much to detrimentally alter the release of the drug should be used to form solid dosage forms of the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition.

Suitable disintegrants that may be used to form solid dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinised starch, other starches, clays, other algins, other celluloses, gums and mixtures thereof.

Suitable lubricants for use with solid dosage forms Include, but are not limited to, calcium stearate, magnesium stearate, mineral oil, light mineral oil, glycerine, sorbitol, mannitol, polyethylene glycol, other glycols, stearic acid, sodium lauryl sulphate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants Include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. A lubricant may optionally be added, typically in an amount of less than about 1 weight percent of the pharmaceutical composition.

Preferably, each solid dosage form contains from about 5 mg to about 3000 mg of the compound of the invention. Preferably, each solid dosage form contains about 5 mg, about 25 mg, about 100 mg, about 200 mg, about 250 mg, or about 500 mg of the compound of the invention. Solid dosage forms suitable for oral administration preferably contain from about 5 mg to about 200 mg the compound of the invention.

The liquid forms in which the novel compositions of the present invention may be incorporated for administration orally include aqueous solutions, suitably flavoured syrups, aqueous, and flavoured emulsions with edible oils such as corn oil, cottonseed oil, sesame oil, coconut oil, or peanut oil, as well as elixirs and similar pharmaceutical vehicles.

Furthermore, the pharmaceutical compositions containing one or more compound(s) of this invention can be administered in combination any other suitable drug, for example for the treatment of gastro-intestinal disorders. When the combination therapy is employed, the pharmaceutical composition containing the compound(s) of this invention and the second drug may be administered simultaneously, sequentially or separately. Each component used in the combination therapy is employed in an amount sufficient for its intended purpose. For example, the secondary drug is employed in sufficient amounts to effect reduction of symptom in question in vivo.

Preferably, the dose range for compounds of this invention is from about 1 mg to about 1000 mg per dose, more preferably about 2 mg to about 500 mg, even more preferably about 5 mg to about 100 mg, and still more preferably about 5 mg to about 60 mg. Again, the particular dose used will depend on the patient (age, weight, etc.), and the severity of the disease (mild, moderate, severe). Lastly, a pharmaceutical composition containing two active ingredients can also be prepared for administering the drugs simultaneously.

The administration of the present drug(-s) will normally take place in connection with food intake, when lipase-colipase are set free due to digestion and an optimal inhibition will be obtained below duodenum.

EXAMPLES

Figure 1A:
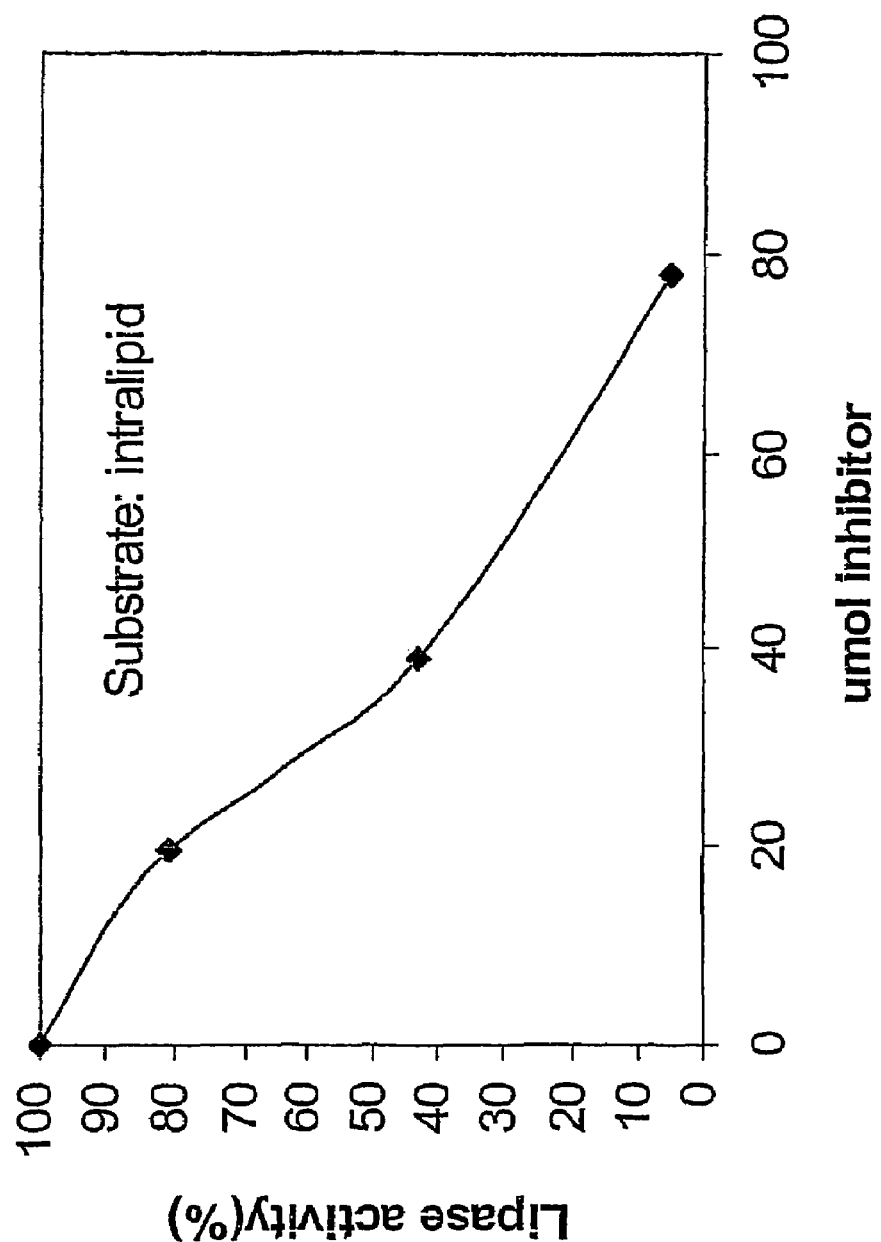
FIGS. 1A and 1B are graphs illustrating lipase activity.
Figure 1B:
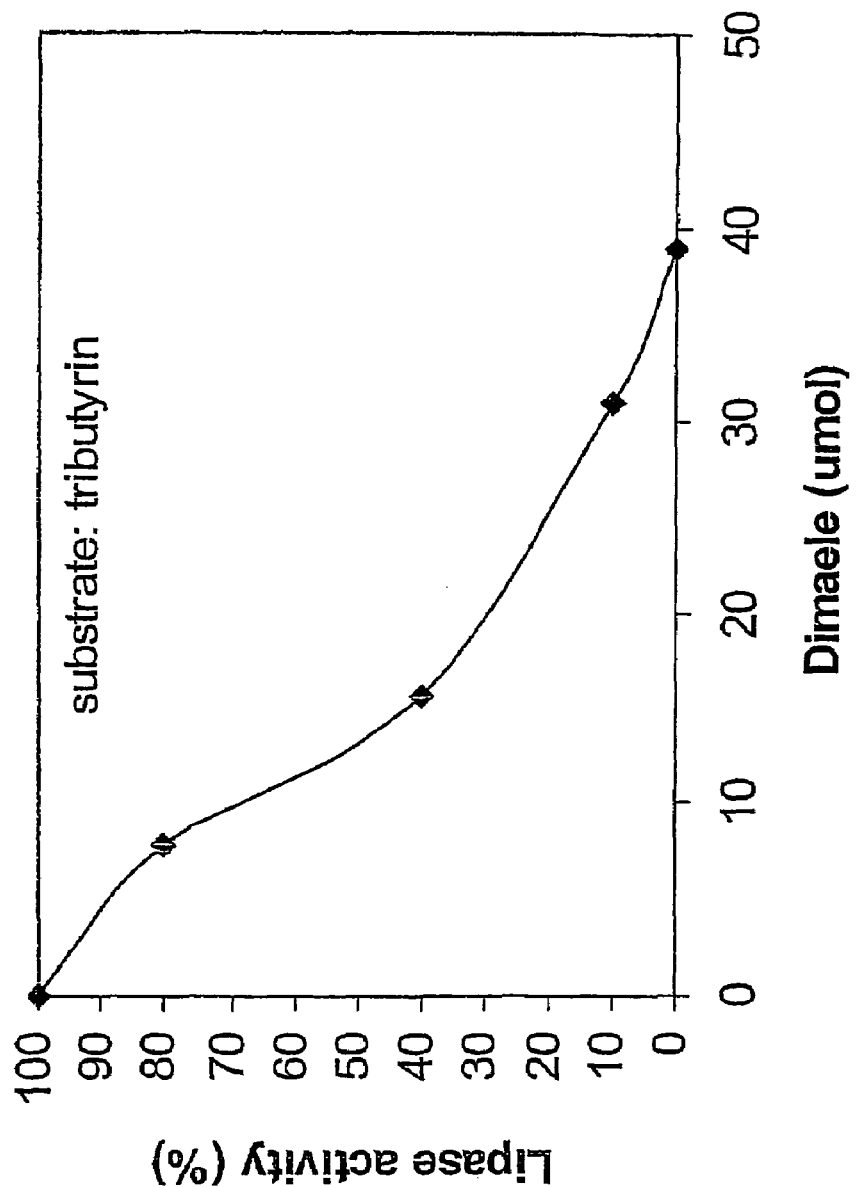
Figure 2A:
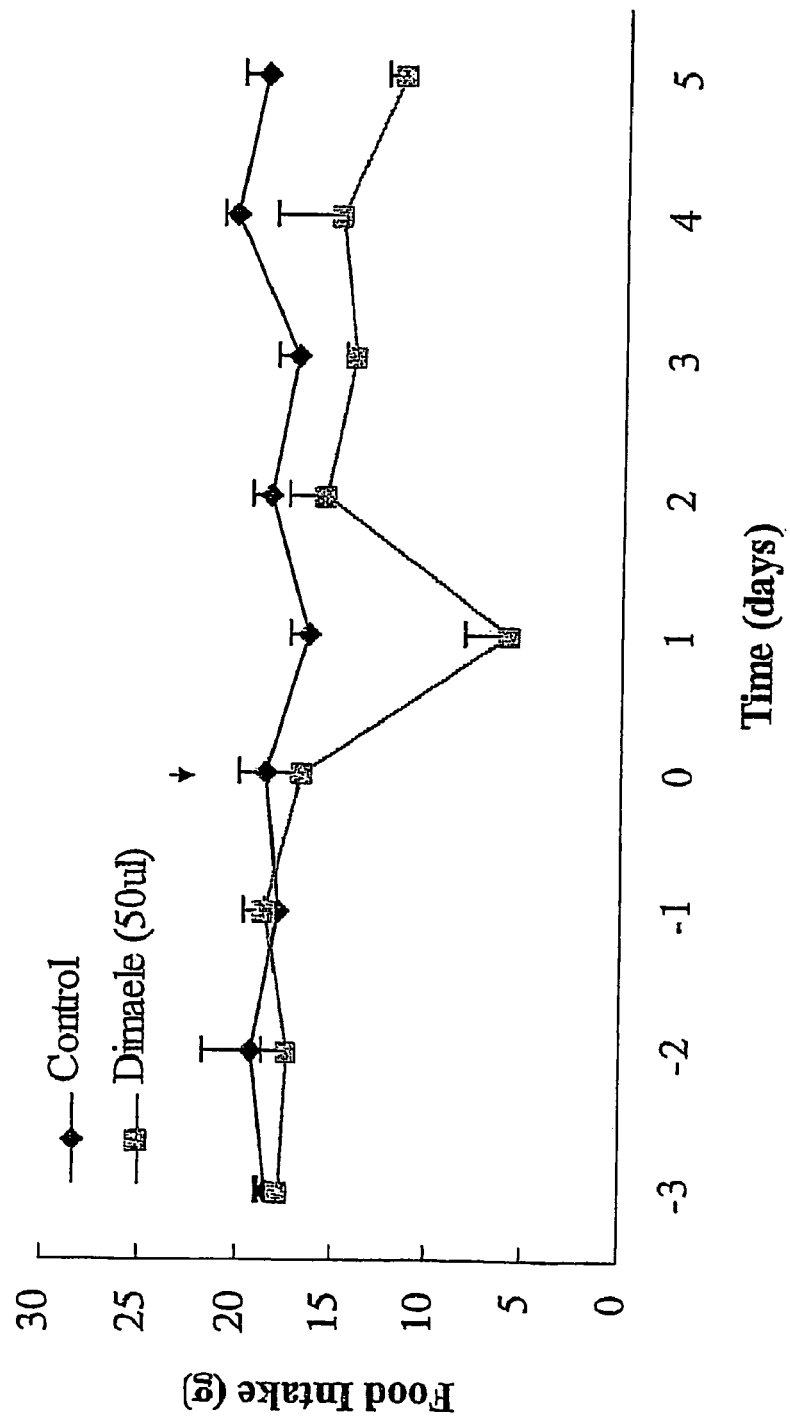
FIGS. 2A and 2B are graphs illustrating the food intake (g) of rats.
Figure 2B:
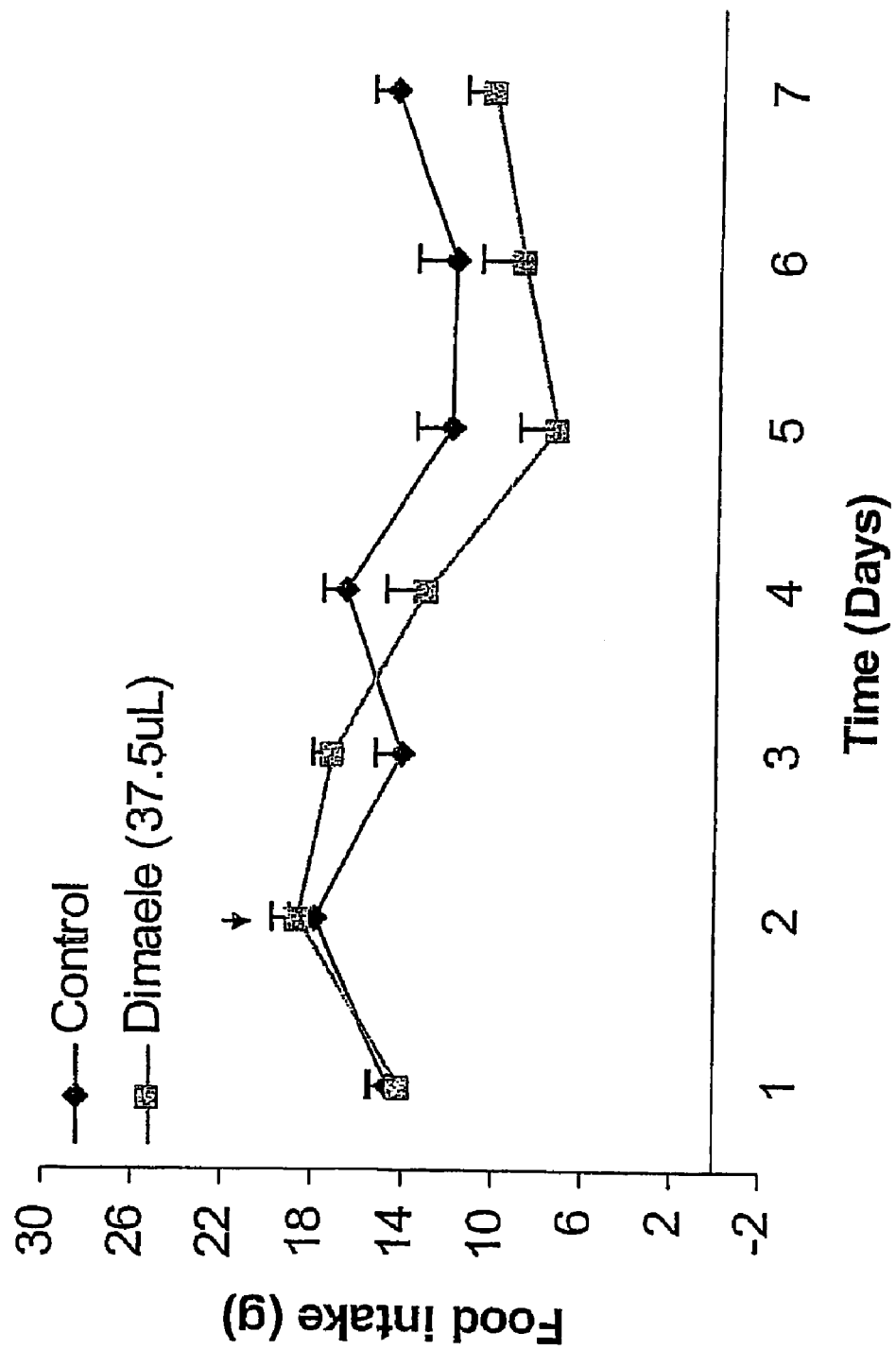
Figure 3:
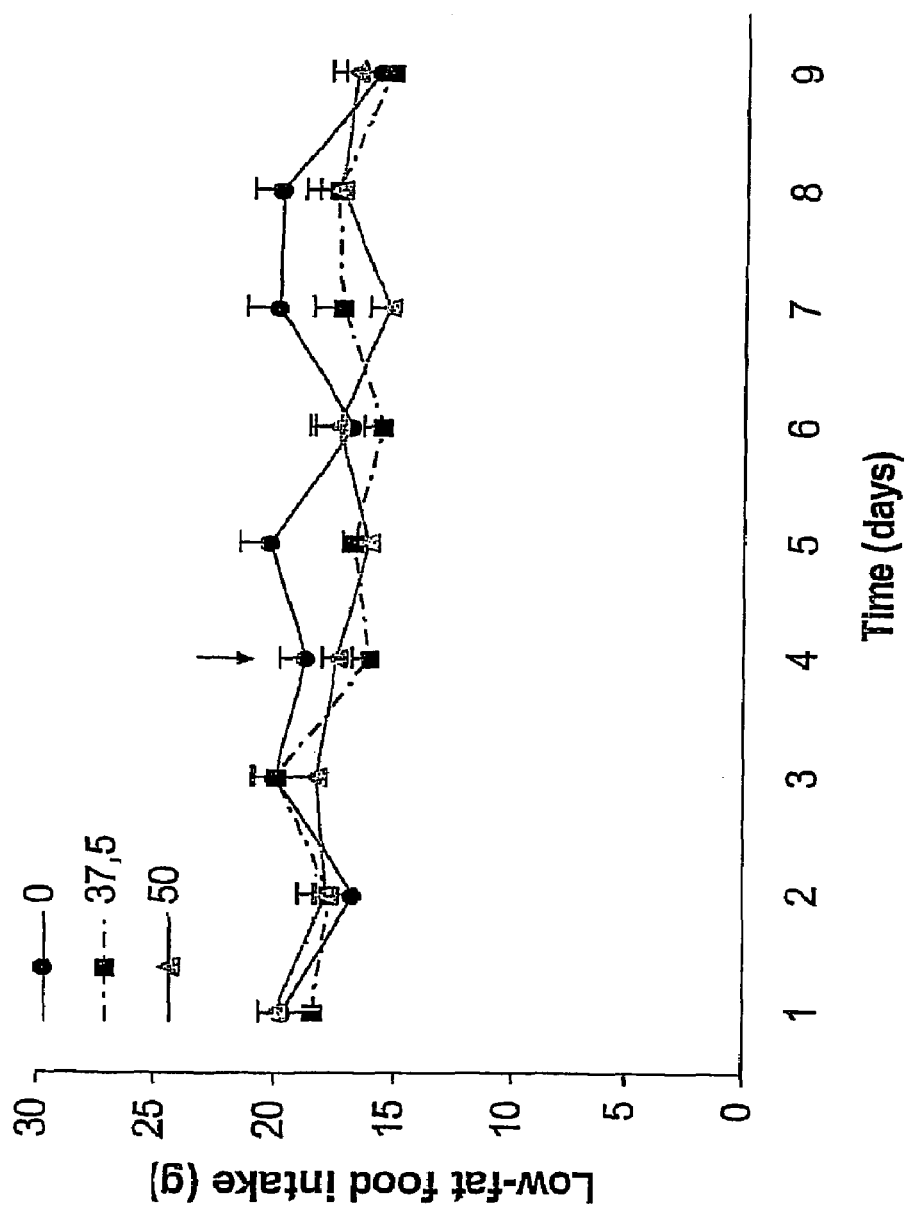
FIG. 3 is a graph illustrating the low-fat food intake (g) of rats.
Figure 4:
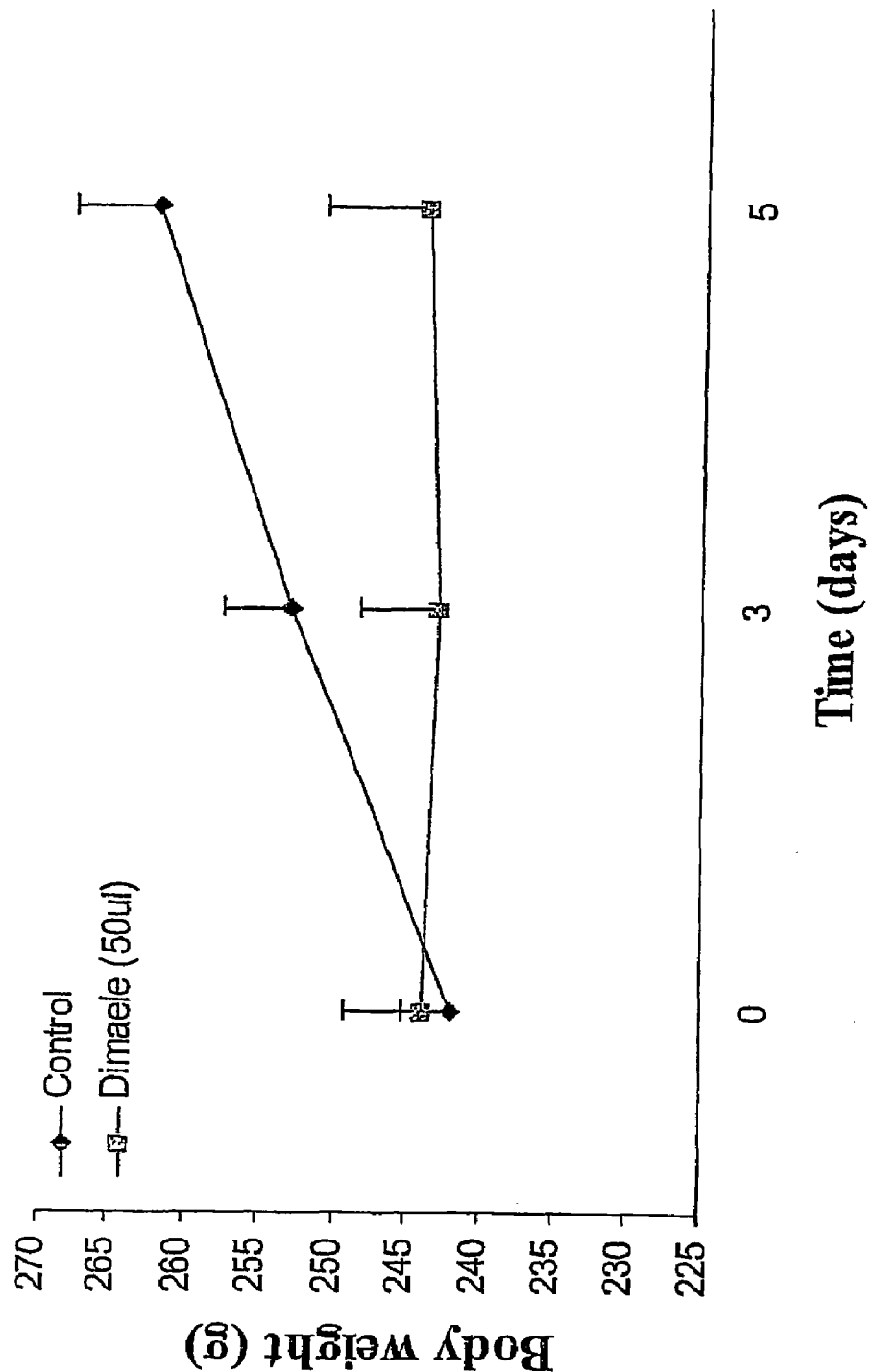
FIG. 4 is a graph illustrating the body weight (g) of rats.
Figure 5A:
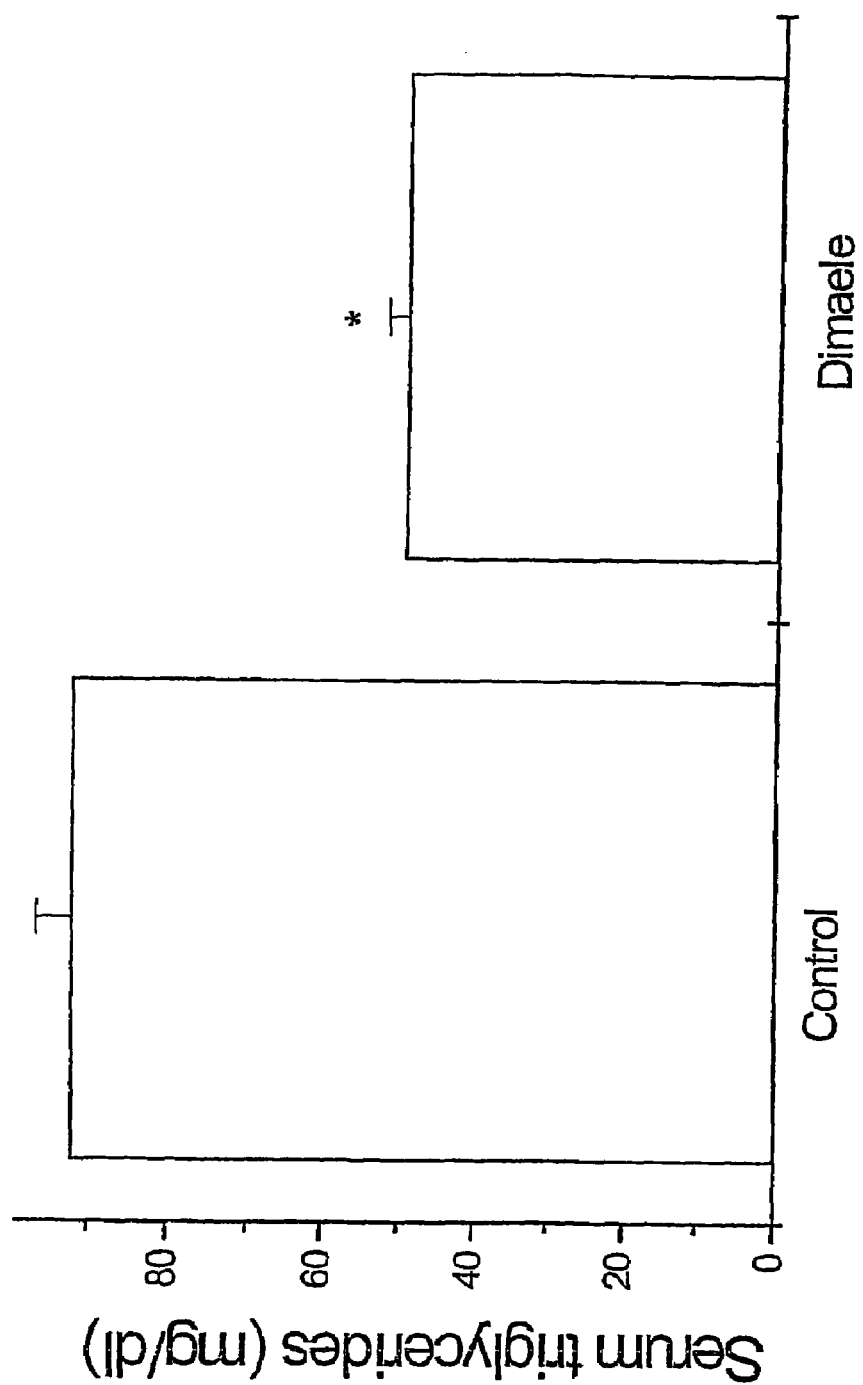
FIGS. 5A and 5B are graphs illustrating the amount of Serum triglycerides (mg/dl) and Serum FFA (mmol/l), respectively, in rats.
Figure 5B:
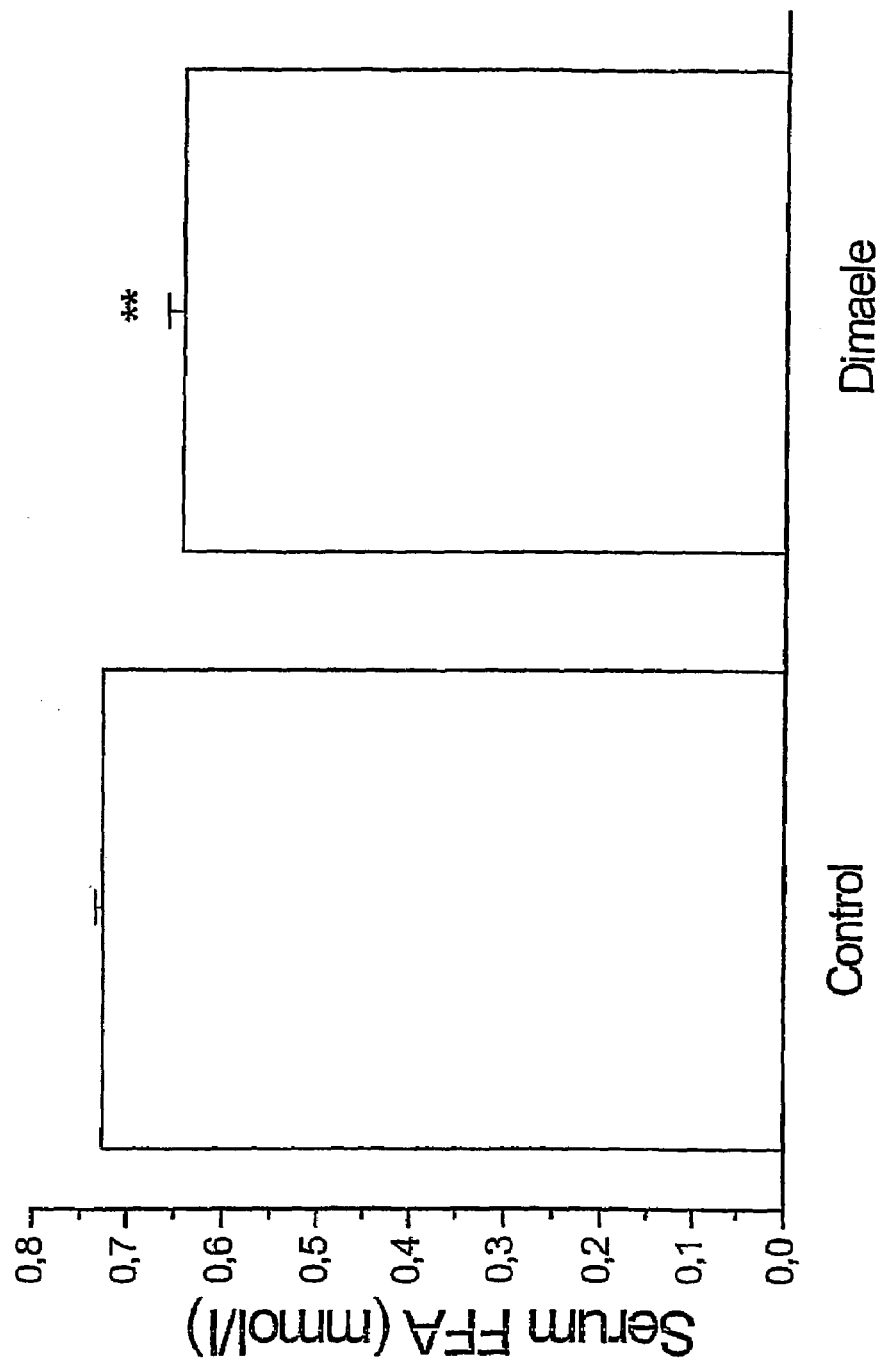
Figure 6A:
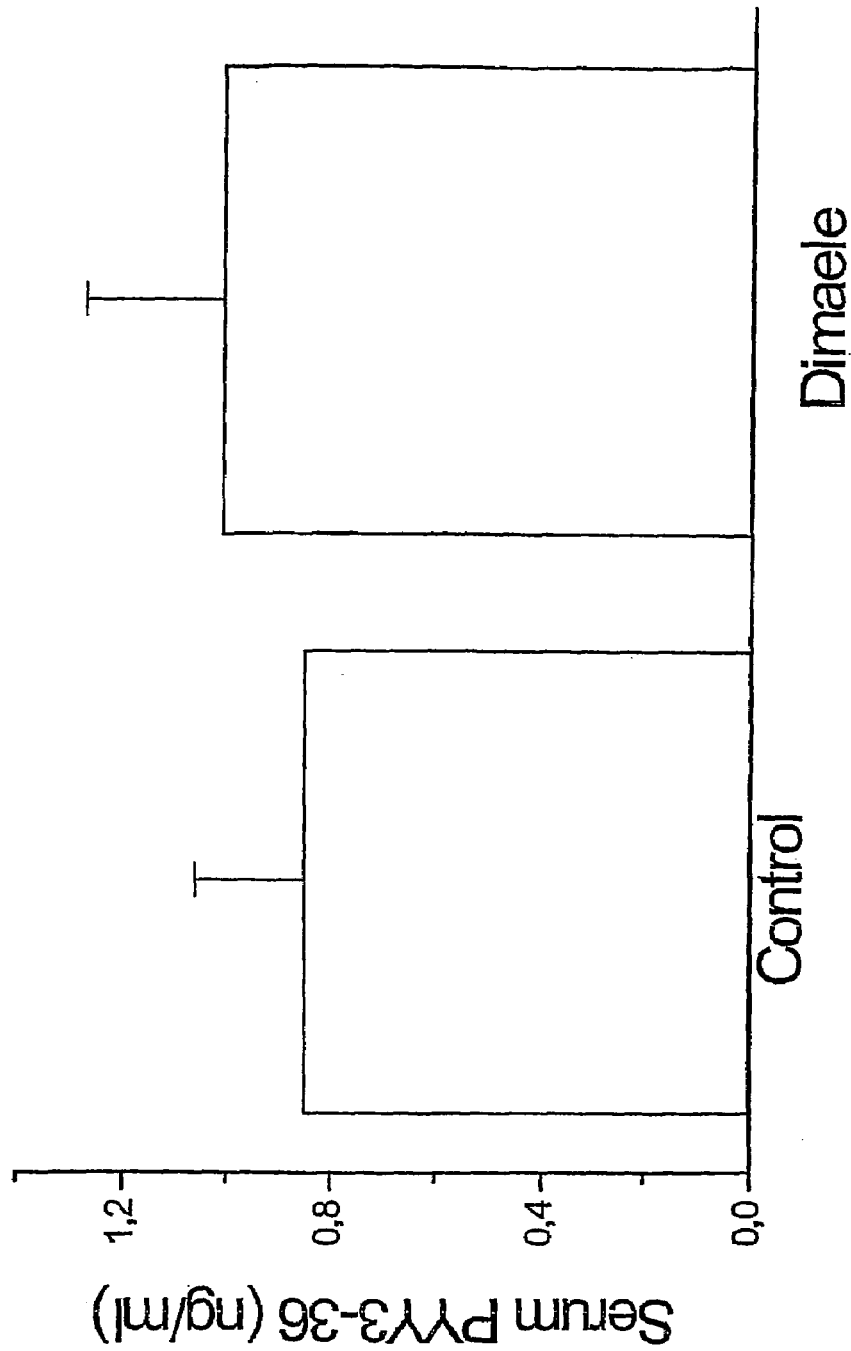
FIGS. 6A, 6B and 6C are graphs illustrating the amount of Serum PYY3-36 (ng/ml), Serum leptin (pmol/l), and Serum ghrelin (pmol/l); respectively, in rats.
Figure 6B:
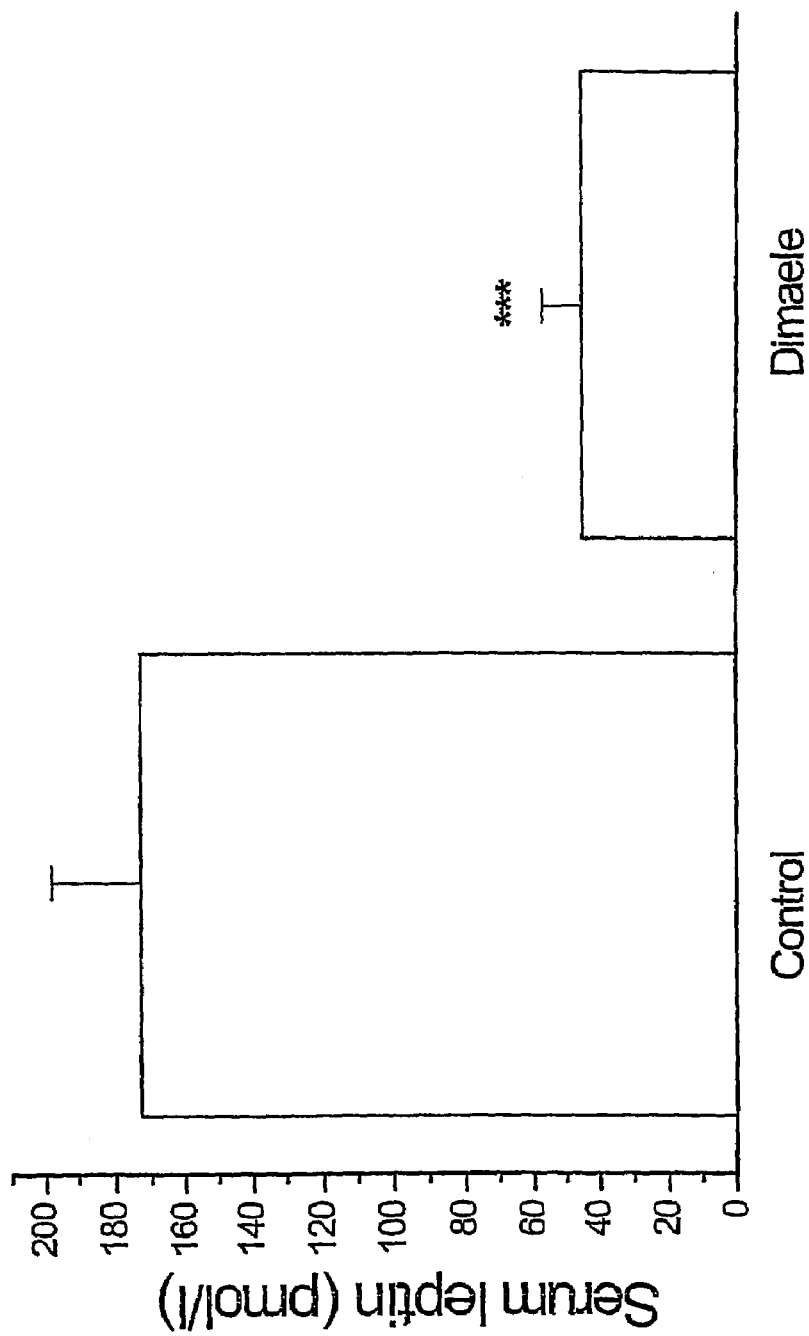
Figure 6C:
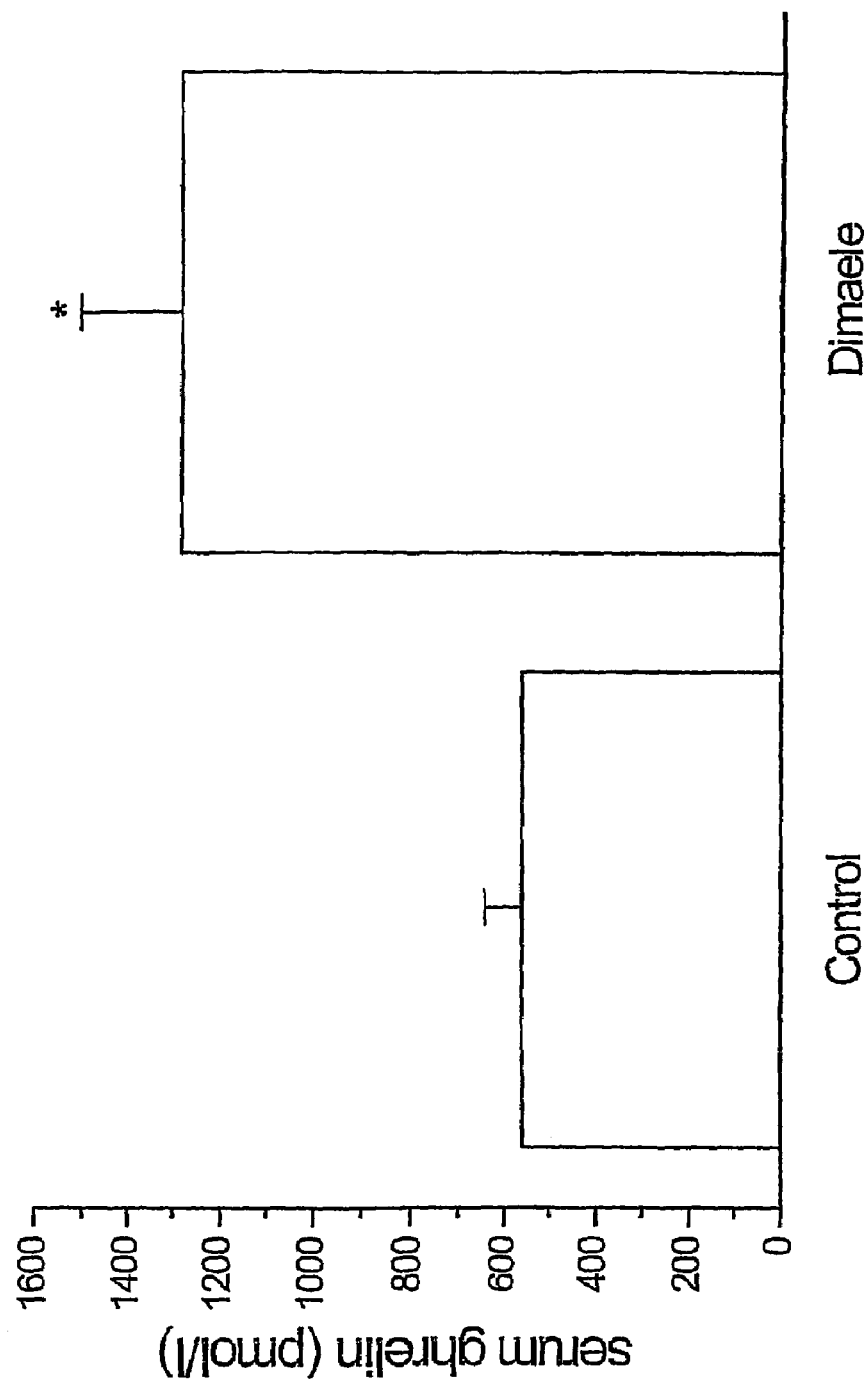
Figure 7:
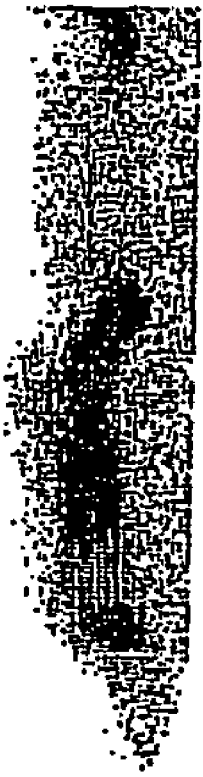
FIG. 7 shows protein expression in rats administered Dimaele.
Figure 8A:
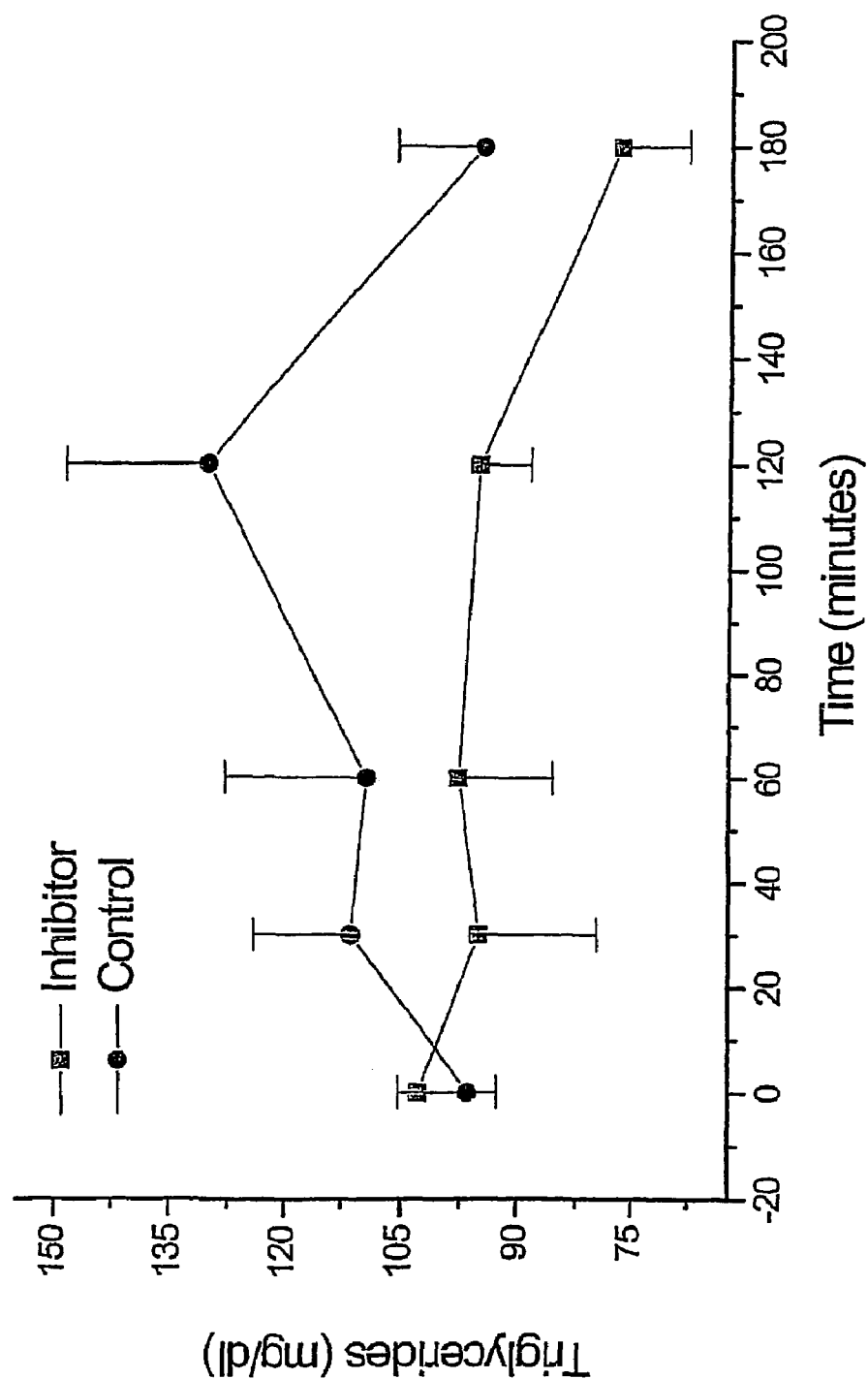
FIGS. 8A and 8B are graphs illustrating the amount of triglycerides (mg/dl) and FFA (mmol/l), respectively, in rats.
Figure 8B:
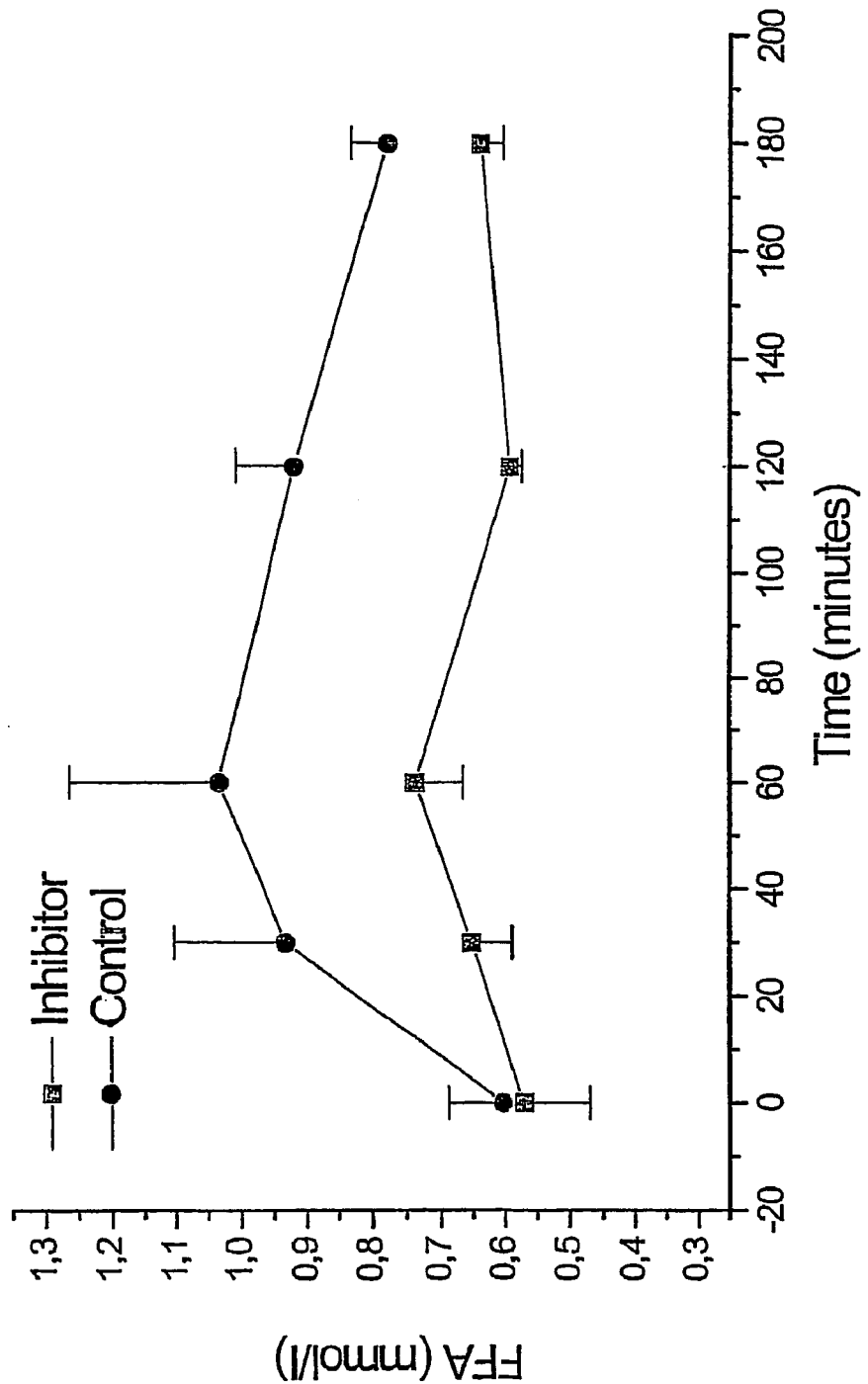

The following preparations and examples are given to enable those skilled in the art to more clearly understand and to practice the present invention. They should not be considered as limiting the scope of the invention, but merely as being illustrative and representative thereof.

Formulation Examples

Example 1

Hard gelatine capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatine capsules In 340 mg quantities.

Example 2

A tablet Formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120.0 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50 to 60° C., and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 4

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatine capsules in 150 mg quantities.

Example 5

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended In the saturated fatty acid glycerides previously melted using the minimum heat necessary. The mixture is then poured into a suppository mould of nominal 2.0 g capacity and allowed to cool.

Example 6

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavour and Colour | q.s. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavour, and colour are diluted with some of the water and added with stirring. Sufficient water is then added to produce the required volume.

Example 7

A formulation may be prepared as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatine capsules in 425.0 mg quantities.

Other suitable formulations for use in the present invention can be found in Remington's Pharmaceutical Sciences, edited by E. W. Martin (Mack Publishing Company, 18th ed., 1990).

The invention claimed is:

1. A method of treating obesity in mammals, including humans, by inhibiting the colipase-lipase interaction by administering a therapeutically effective amount of at least one compound defined by the following general formulae

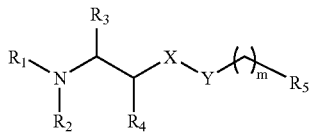

wherein
R₁ and R₂ each independently is hydrogen, or lower alkyl,
R₃ and R₄ each independently is hydrogen, or lower alkyl,
X is —O—, —C— or —S—,
Y is a covalent bound or is $[-CH_2-CH2-O-]_x$, wherein x is an integer from 0 to 8,
m is an integer from 0 to 30,
R₅ is hydrogen, $CH_3$ or $CF_3$ optionally in combination with pharmaceutically inert excipients.

2. A method according to claim 1, wherein X, Y, $(CH_2)_m$ and R₅ together comprises at least 8 carbon atoms.

3. A method according to claim 1, wherein $(CH_2)_m$ comprises one or more double or triple bonds.

4. A method according to claim 1, wherein, the compound is one or more of
2-(Dimethylamino)-ethyl-stearyl ether
2-(Dimethylamino)-ethyl-tetradecyl ether
2-(Dimethylamino)-ethyl-oleyl ether
2-(Dimethylamino)-ethyl-linolyl ether
2-(Dimethylamino)-ethyl-dodecyl ether
2-(Dimethylamino)-ethyl-octyl ether
2-(Diethylamino)-ethyl-stearyl ether
2-(Diethylamino)-ethyl-oleyl ether
2-(Diethylamino)-ethyl-linolyl ether
2-(Diethylamino)-ethyl-dodecyl ether
2-(Diethylamino)-ethyl-octyl ether
2-(Diisopropylamino)-ethyl-stearyl ether
2-(Diisopropylamino)-ethyl-oleyl ether
2-(Diisopropylamino)-ethyl-linolyl ether
2-(Diisopropylamino)-ethyl-dodecyl ether
2-(Diisopropylamino)-ethyl-octyl ether
2-(Dimethylamino)-ethyl-pentaethyleneglycol-stearyl ether
2-(Dimethylamino)-ethyl-pentaethyleneglycol-linolyl ether
2-(Dimethylamino)-ethyl-pentaethyleneglycol-oleyl ether
2-(Dimethylamino)-ethyl-pentaethyleneglycol-dodecyl ether
2-(Dimethylamino)-ethyl-pentaethyleneglycol-octyl ether
2-(Dimethylamino)-ethyl-pentaethyleneglycol butyl ether
2-(Dimethylamino)-ethyl-pentaethyleneglycol methyl ether
2-(Dimethylamino)-ethyl-pentaethyleneglycol ethyl ether
2-(Dimethylamino)-ethyl-triethyleneglycol-dodecyl ether
2-(Dimethylamino)-ethyl-triethyleneglycol-octyl ether
2-(Dimethylamino)-ethyl-triethyleneglycol butyl ether
2-(Dimethylamino)-ethyl-triethyleneglycol methyl ether
2-(Dimethylamino)-ethyl-triethyleneglycol ethyl ether
2-(Dipropylamino)-ethyl-octaethyleneglycol dodecyl ether
2-(Dimethylamino)-ethyl-octaethyleneglycol dodecyl ether
2-(Diethylamino)-ethyl-octaethyleneglycol dodecyl ether
N,N-dimethyl hexadecyl amine
N,N-dimethyl tetradecyl amine
N,N-dimethyl dodecyl amine.

5. The method according to claim 1, wherein x is 0 to 5.
6. The method according to claim 1, wherein m is 4 to 16.
7. The method according to claim 1, wherein m is 4 to 12.

* * * * *